US010058654B2

(12) United States Patent
Gabrielsson

(10) Patent No.: US 10,058,654 B2
(45) Date of Patent: Aug. 28, 2018

(54) POWER UNIT

(71) Applicant: CAREBAY EUROPE LTD, Swatar (MT)

(72) Inventor: Elin Gabrielsson, Hasselby (SE)

(73) Assignee: CAREBAY EUROPE LTD, Sliema (MT)

( * ) Notice: Subject to any disclaimer, the term of this patent is extended or adjusted under 35 U.S.C. 154(b) by 253 days.

(21) Appl. No.: 14/909,800

(22) PCT Filed: Jul. 7, 2014

(86) PCT No.: PCT/EP2014/064457
§ 371 (c)(1),
(2) Date: Feb. 3, 2016

(87) PCT Pub. No.: WO2015/018578
PCT Pub. Date: Feb. 12, 2015

(65) Prior Publication Data
US 2016/0193413 A1    Jul. 7, 2016

(30) Foreign Application Priority Data
Aug. 8, 2013    (SE) ...................................... 1350946

(51) Int. Cl.
*A61M 5/20*    (2006.01)
*A61M 5/32*    (2006.01)

(52) U.S. Cl.
CPC ........ *A61M 5/2033* (2013.01); *A61M 5/3204* (2013.01); *A61M 2005/206* (2013.01); *A61M 2005/208* (2013.01)

(58) Field of Classification Search
CPC .............. A61M 5/2033; A61M 5/3204; A61M 2005/206
See application file for complete search history.

(56) References Cited

U.S. PATENT DOCUMENTS

| 5,658,259 A * | 8/1997 | Pearson .............. A61M 5/2033 604/136 |
| 2005/0101919 A1 * | 5/2005 | Brunnberg .......... A61M 5/2033 604/197 |

FOREIGN PATENT DOCUMENTS

| EP | 2489380 | 8/2012 |
| WO | 2011/005177 | 1/2011 |

OTHER PUBLICATIONS

International Search Report and Written Opinion for Int. App. No. PCT/EP2014/064457, completed Sep. 18, 2014.

* cited by examiner

*Primary Examiner* — Laura Bouchelle
*Assistant Examiner* — Tasnim M Ahmed
(74) *Attorney, Agent, or Firm* — McDonnell Boehnen Hulbert & Berghoff LLP

(57) ABSTRACT

A medicament delivery device is provided having a power body having opposite proximal and distal ends, a plunger rod driver coaxial and movably arranged in relation to said power body, a plunger rod coaxial and movably arranged in relation to said plunger rod driver, a force spring element operably connected between the plunger rod and the power body The plunger rod driver has a first holding elements arranged to interact with second holding elements on the plunger rod and with the power body for releasably holding the plunger rod with the force spring element in an injection tensioned state.

16 Claims, 14 Drawing Sheets

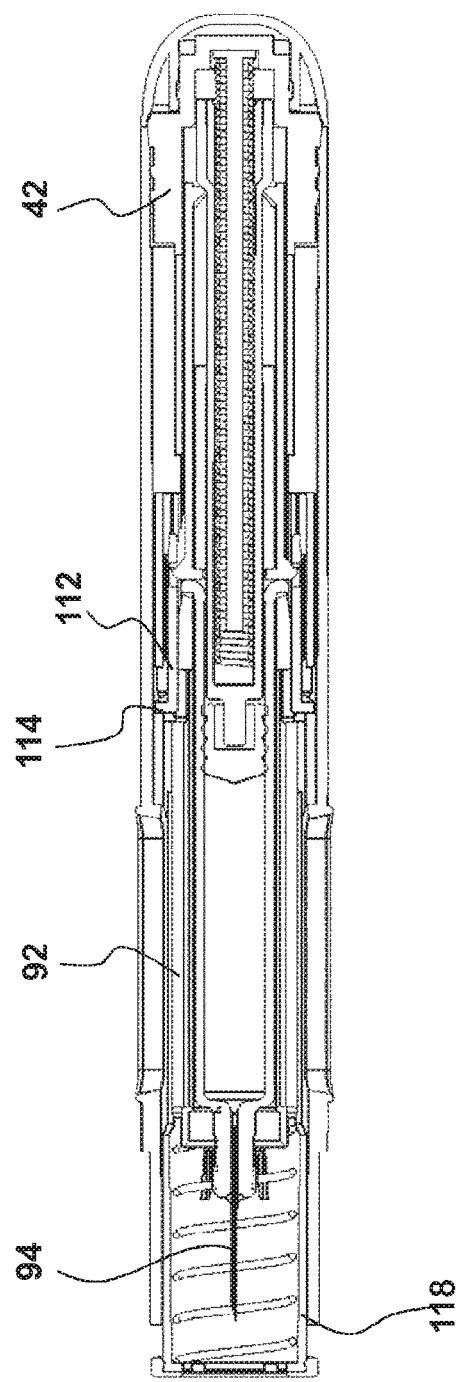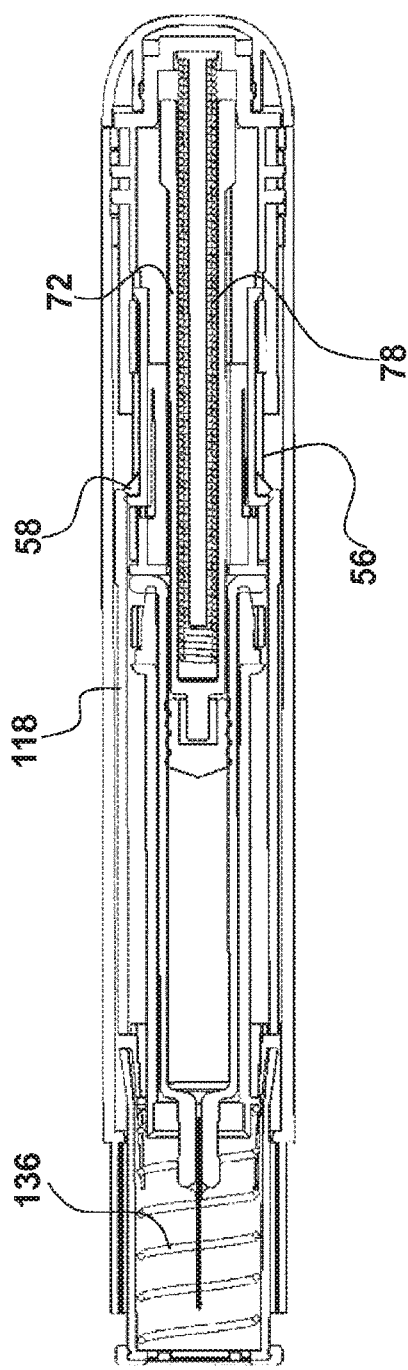

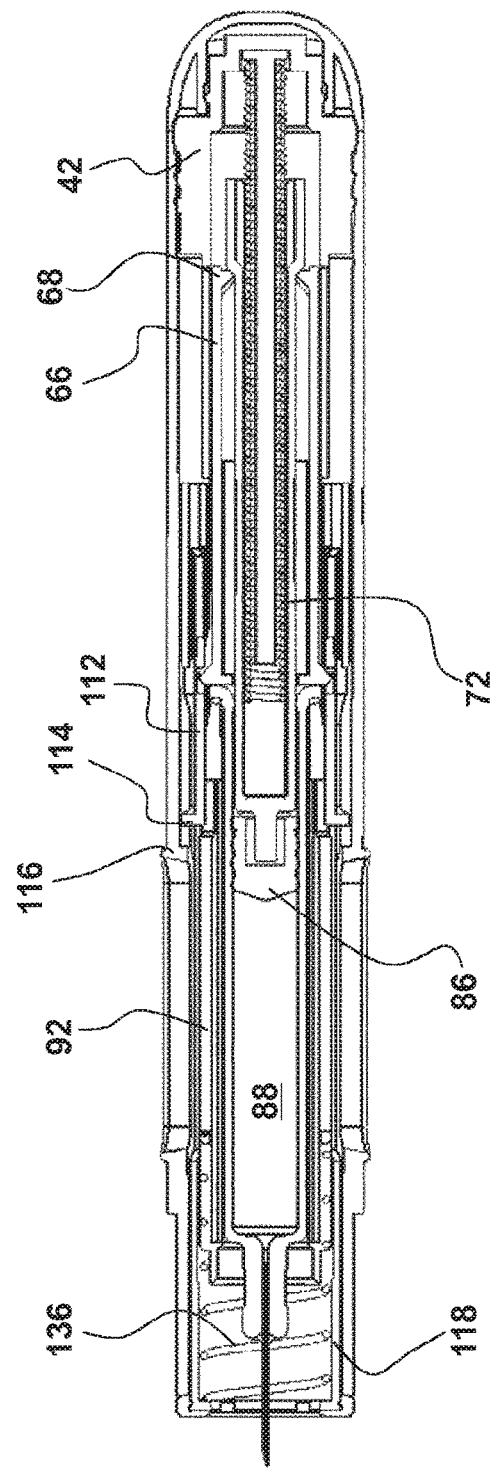
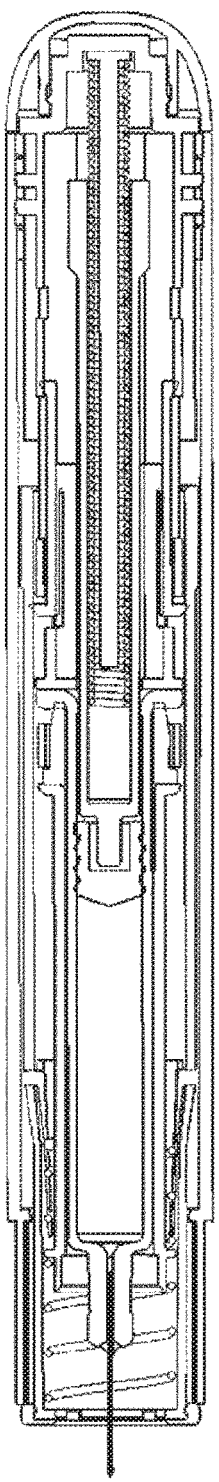
Fig. 12a
Fig. 12b

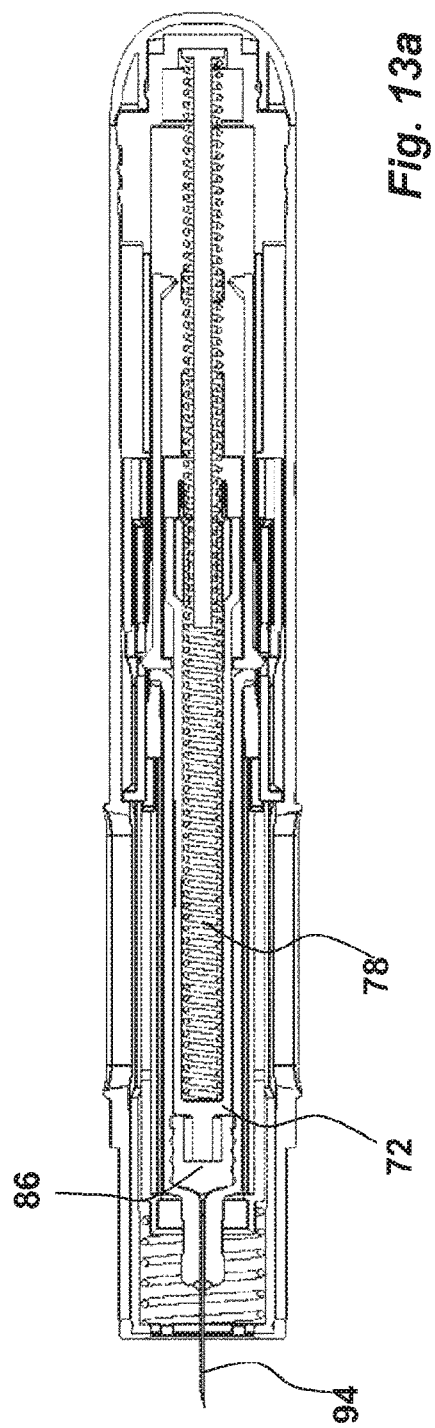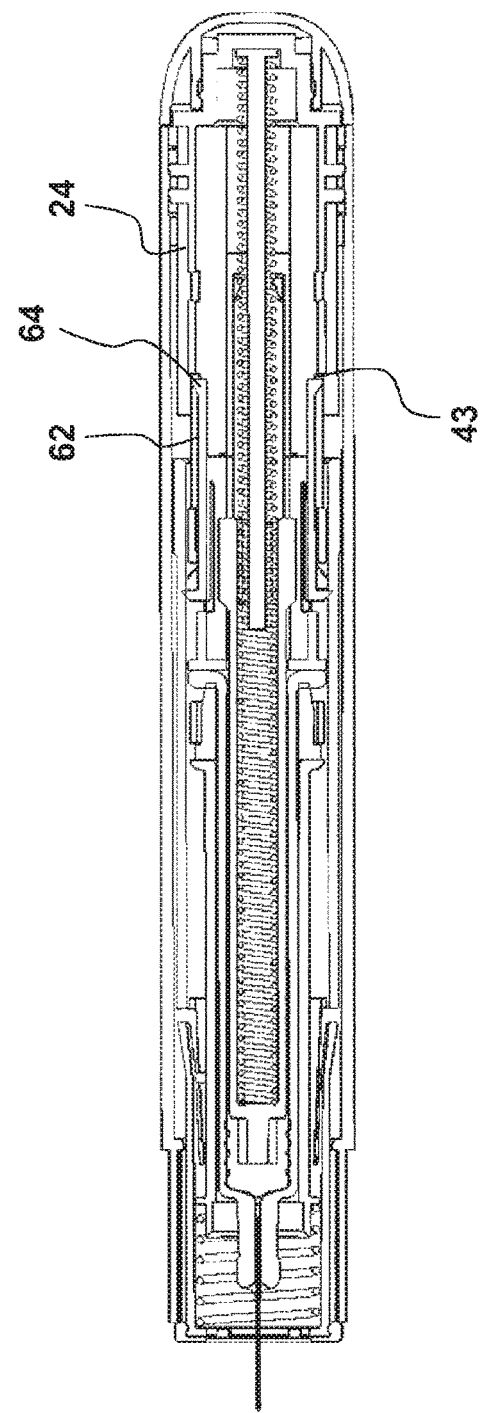

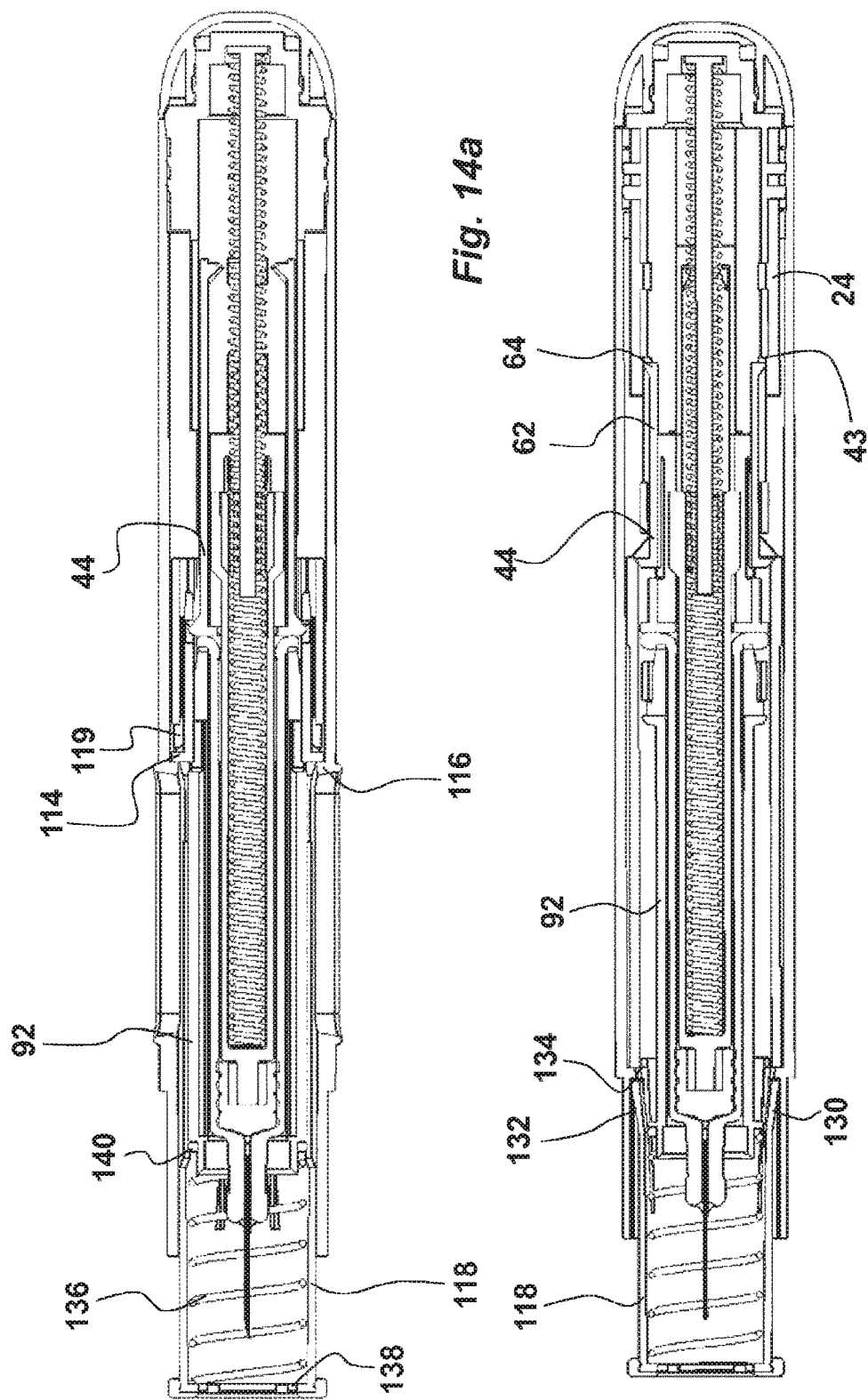

POWER UNIT

CROSS REFERENCE TO RELATED APPLICATIONS

The present application is a U.S. National Phase Application pursuant to 35 U.S.C. § 371 of International Application No. PCT/EP2014/064457 filed Jul. 7, 2014, which claims priority to Swedish Patent Application No. 1350946-8 filed Aug. 8, 2013. The entire disclosure contents of these applications are herewith incorporated by reference into the present application.

TECHNICAL AREA

The present invention relates to a power unit intended to be arranged in a medicament delivery device, which medicament delivery device is arranged with a number of automatic functions in order to facilitate the delivery of a dose of medicament from the device to a user.

BACKGROUND

Many medicament delivery devices are arranged with a number of automatically triggered functions such as penetration, injection, withdrawal and/or protection of a medicament delivery member after delivery, just to mention a few.

Many of these functions require a number of components, making the device rather complex, as well as requiring handling aspects that may be difficult to perform for some users, even though the functions as such are automatic. There are also aspects regarding the interaction between different components requiring handling tolerance chains that may be quite complex when a number of components are to interact.

In many devices it is thus a preferred to keep the number of components as low as possible in order to reduce the complexity of the functions as well as reducing the tolerance chains. Also in view of handling and administration of medicament the number of components of the device should be kept as low as possible in order to provide a clear and concise operation. Regarding manufacturing aspects, it is also often desired to have as few components as possible and/or to provide several functions in one component.

In order to keep the number of components as low as possible, some devices use one single spring for both a penetration operation as well as a subsequent injection operation. A common solution is then to let the single spring act on a plunger rod, which in turn acts on a stopper inside a medicament container. The plunger rod then pushes the medicament container in the proximal direction in order to perform a penetration.

The movement in the proximal direction is possible because the medicament is incompressible and because the passage through the medicament delivery member is very small. However, some medicament will be expelled during penetration, which may be a clear drawback for some treatments where it is important that the medicament is delivered at a certain predetermined depth of penetration.

In all, there is room for improvements in the area of medicament delivery devices arranged with several functions.

SUMMARY

As used herein, the term "liquid" encompasses all solutions, suspensions, emulsions, oils, gels and so forth, which generally behave as liquids at operating temperatures. The term explicitly includes solid compositions dissolved or dispersed in a liquid carrier. Materials behaving as highly viscous liquids are also included.

In the present application, when the term "distal part/end" is used, this refers to the part/end of the medical delivery device, or the parts/ends of the members thereof, which under use of the device are located the furthest away from the delivery site of the patient. Correspondingly, when the term "proximal part/end" is used, this refers to the part/end of the device, or the parts/ends of the members thereof, which under use of the device are located closest to the delivery site of the patient.

The aim of the present invention is to remedy the above mentioned drawbacks of the state of the art. This aim is obtained by the features of the independent patent claim. Preferable embodiments of the invention form the subject of the dependent patent claims.

According to a favourable solution, it discloses a power unit for a medicament delivery device. The power unit may comprise a power body having opposite proximal and distal ends. Preferably the power body may be fixedly arranged to a housing of a medicament delivery device. The power body may further be generally tubular and be arranged in a longitudinal direction of the medicament delivery device.

Further, the power unit may comprise a coaxial plunger rod driver, which plunger rod driver is coaxially and movably arranged in relation to said power body. Also the plunger rod driver may be generally tubular in shape. The plunger rod driver may be arranged partial coaxially inside the power body. A further favourable component of the power unit is a plunger rod. The plunger rod may also be arranged coaxially and movably arranged in relation to said plunger rod driver along the longitudinal direction of the device in which the power unit is to be arranged. The plunger rod may be arranged partial coaxially inside the plunger rod driver.

In order to move the plunger rod in the longitudinal direction, more specifically towards the proximal end, a force spring element may advantageously be operably connected between said plunger rod and said power body.

According to a favourable embodiment, the plunger rod driver may comprise a first holding element arranged to interact with a second holding element on the plunger rod and with the power body, more specifically with a wall of the power body, for releasibly holding the plunger rod with the force spring element in an injection tensioned state. The plunger rod is then ready to be released and to be driven by the tensioned force spring element. The first and second holding elements cooperate to provide a powered and ready to use power unit for an injection sequence. The first holding element may in one favourable embodiment comprises a distally directed flexible arm having a protrusion at its free end, more particularly a radially inwards directed protrusion, and wherein the second holding element comprises a contact surface such that contact surface rest on the protrusion of the distally directed flexible arm.

Also according to a feasible solution, the plunger rod driver may comprise a third holding element arranged to interact with a fourth holding element on said power body for releasibly holding said plunger rod driver in a penetration tensioned state. The plunger rod driver is then also ready to be activated and to be driven by the tensioned force spring element, wherein the third and the fourth holding elements cooperate to provide a powered and ready to use power unit for a penetration sequence. The third holding element may also preferably comprise a flexible tongue having a protrusion, more particularly a radially outwards directed protrusion, wherein the fourth holding element comprises a contact surface, more particularly a transversal and distally directed end contact surface provided on an elongated opening on the power body, such that the radially outwards directed protrusion may rest on the transversal and distally directed end contact surface.

Thus, the plunger rod driver is configured to be coaxially arranged within the power body such that the wall of the power body prevents the first holding element of the plunger rod driver to flex radially outwards whereby the protrusion of the first holding element is held in contact with the second holding element for holding the plunger rod and said force spring element in the injection tensioned state and wherein the third holding element of the plunger rod driver is configured to be resting on the forth holding element of the power body for holding the plunger rod driver in the penetration tensioned state.

The plunger rod driver of the power unit may preferably further comprises a first attachment element arranged to interact with a second attachment element on a medicament container holder of a medicament delivery device. With this solution the plunger rod driver and the medicament container holder may be interconnected to operably act as one single unit. The first attachment element may comprise at least one locking protrusion on a proximal area of the plunger rod driver and the second attachment member comprises at least one flexible arm provided with a recess, arranged to accommodate said at least one locking protrusion.

According to a further favourable aspect of the power unit, the plunger rod driver may further be arranged with a first blocking element arranged to interact with a second blocking element on said power body for blocking any movement of said plunger rod driver in the distal direction after the plunger rod driver is released from the penetration tensioned state. The first blocking element may comprise a flexible arm having a protrusion and the second blocking element may comprise a transversal and proximally directed end contact surface provided on an elongated opening of the power body.

With this solution, any movement of said plunger rod driver in the distal direction is blocked after the plunger rod driver is released from the penetration tensioned state. The plunger rod driver is then driven by the force spring element to a certain position in a proximal direction, after which the plunger rod driver is locked from being moved back in the distal direction. It may then act as a fixed part that components of subsequent sequences and/or functions may utilize.

According to a favourable embodiment, it may comprise a medicament delivery device, comprising the power unit according to the invention. The power unit may then be arranged inside a generally tubular housing having opposite proximal and distal ends along a longitudinal axis (L). Further, the medicament delivery device may comprise a medicament container holder capable of supporting a medicament container provided with a medicament delivery member where the medicament container comprises a chamber containing a medicament, and an axially movable stopper.

The medicament delivery device may also comprise a generally tubular medicament delivery member shield coaxially and slidably arranged within the housing, wherein the medicament delivery member shield may be provided with a medicament delivery member shield force element operably arranged to force the medicament delivery member shield in the proximal direction.

According to another favourable solution, the medicament delivery member shield may be arranged with flexible first locking elements, which first locking elements may be arranged extending in a generally distal direction, operably engageable with second locking elements arranged to said housing. Then the first and the second locking elements may be arranged to engage and lock the medicament delivery member shield when the medicament delivery member shield force element has urged said medicament delivery member shield in the proximal direction after medicament delivery, thereby shielding said medicament delivery member. With this solution a very sturdy and secure shielding of the medicament delivery member is obtained, greatly reducing the risk of accidental injuries caused by the medicament delivery member.

Further, the first locking elements comprise at least two tongues having free ends being flexible in a direction which is generally perpendicular to the longitudinal axis (L). The first locking elements are arranged with a certain inclination which extends outwardly in relation to the longitudinal axis. Each second locking element comprises at least one proximally directed ledge portion having one recess into which said first locking elements fit for engagement.

The generally tubular medicament delivery member shield is configured to interact with the third holding elements which are resting on the fourth holding elements when the tubular medicament delivery member shield is moved in the distal direction in relation to the housing such that the third holding element are forced to move generally inwards whereby the plunger rod driver is released from the penetration tensioned state.

Further, the plunger rod driver together with the plunger rod are movable in relation to the power body such that after the plunger rod driver is released from the penetration tensioned state, the first blocking elements are moved out into openings of the power body for interacting with the second blocking elements whereby the medicament container holder and the plunger rod driver are prevented from moving in the distal direction by the medicament delivery member shield force element. Also the plunger rod driver together with the plunger rod are movable in relation to the power body such that after the plunger rod driver is released from the penetration tensioned state, the first holding elements of the plunger rod driver are moved out of the wall of the power body and flexed radially outwards whereby the first holding elements of the plunger rod driver are moved out of contact with the second holding element for releasing the plunger rod with said force spring element from the injection tensioned state.

These and other aspects of and advantages will become apparent from the following detailed description and from the accompanying drawings.

BRIEF DESCRIPTION OF DRAWINGS

In the following detailed description of the invention, reference will be made to the accompanying drawings, of which

DETAILED DESCRIPTION

Figure 1:
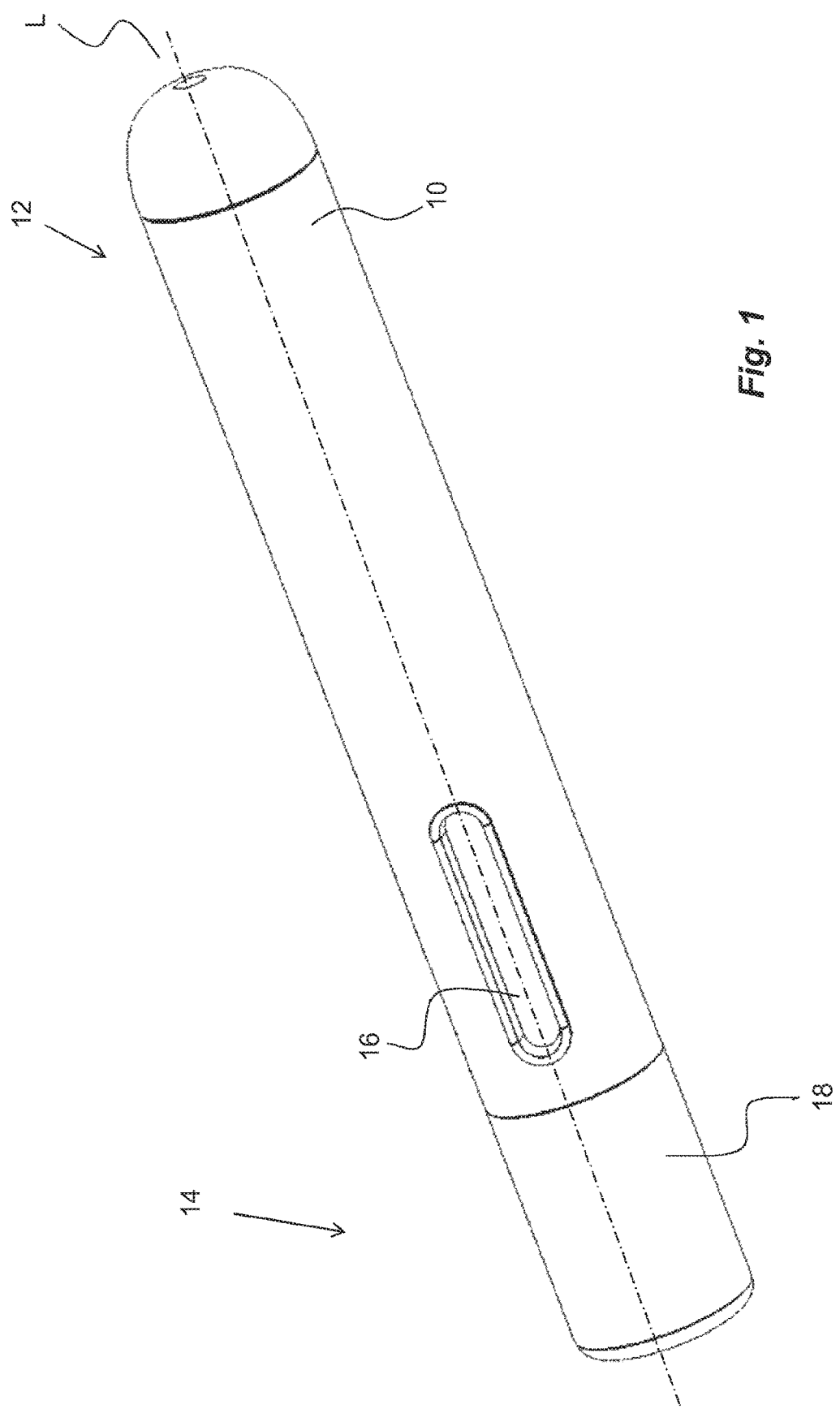
FIG. 1 shows a perspective view of an embodiment of a medicament delivery device.

The embodiment shown in the drawings comprises a generally tubular elongated housing 10 having a distal end 12 and a proximal end 14 along a longitudinal axis L, FIG. 1. The housing is arranged with openings or windows 16 in a proximal area of the housing. At the proximal end a protective cover or cap 18 is arranged to be releasibly attached to the proximal end of the housing and at the distal end an end cap 26. There are a number of different attachment means that could be utilized, such as a mere frictional press fit, to mechanical members interacting with each other. In the interior of the housing 10 a power unit 20 is arranged at a distal end thereof and a medicament delivery unit 22 is arranged at a proximal end of the housing, FIG. 3a.

Figure 4:
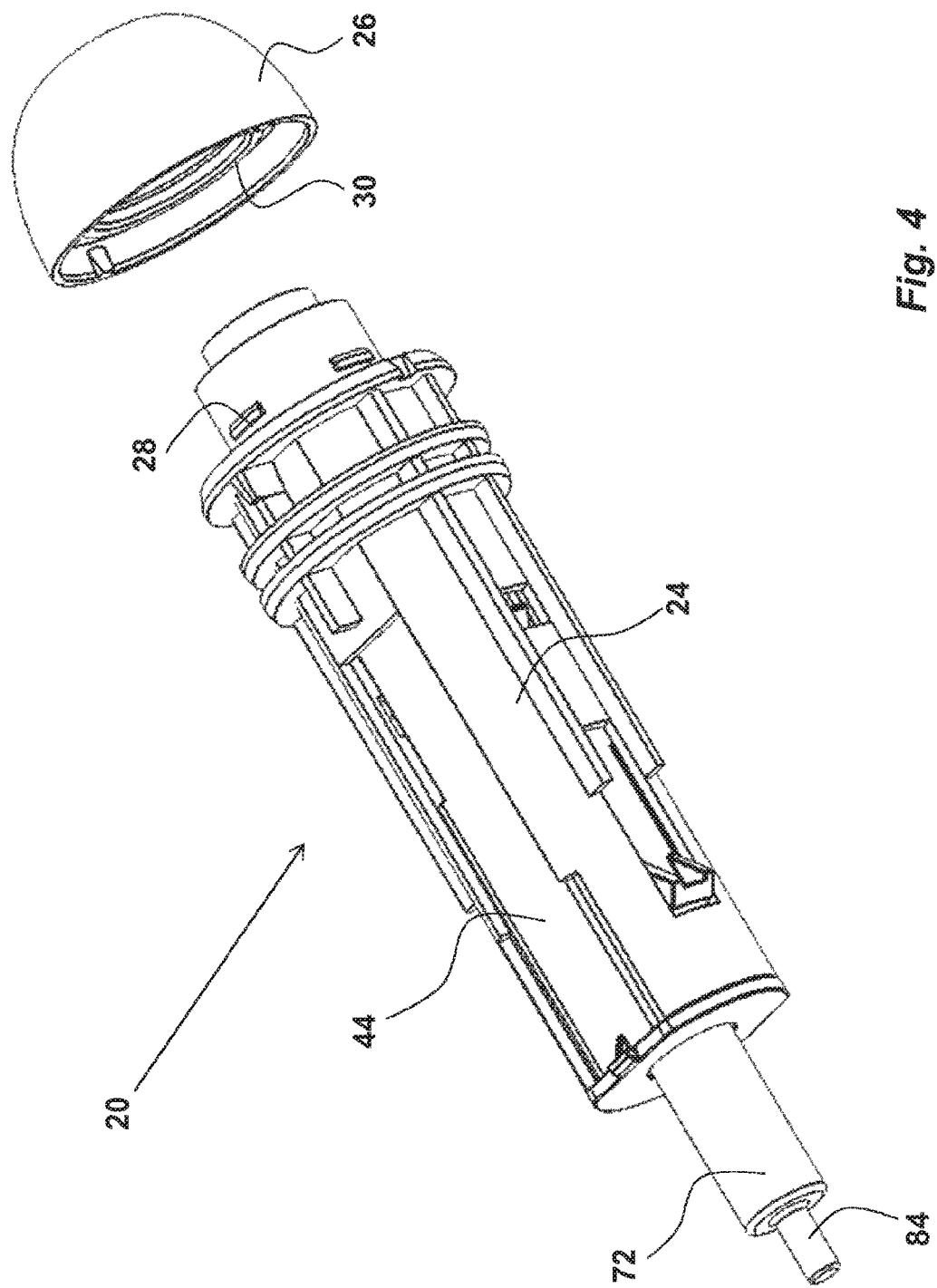
FIGS. 4-10 show detailed views of components comprised in the device of FIG. 1, and FIGS. 11-14 show cross-sectional views of the device of FIG. 1 in different functional states.
Figure 5:
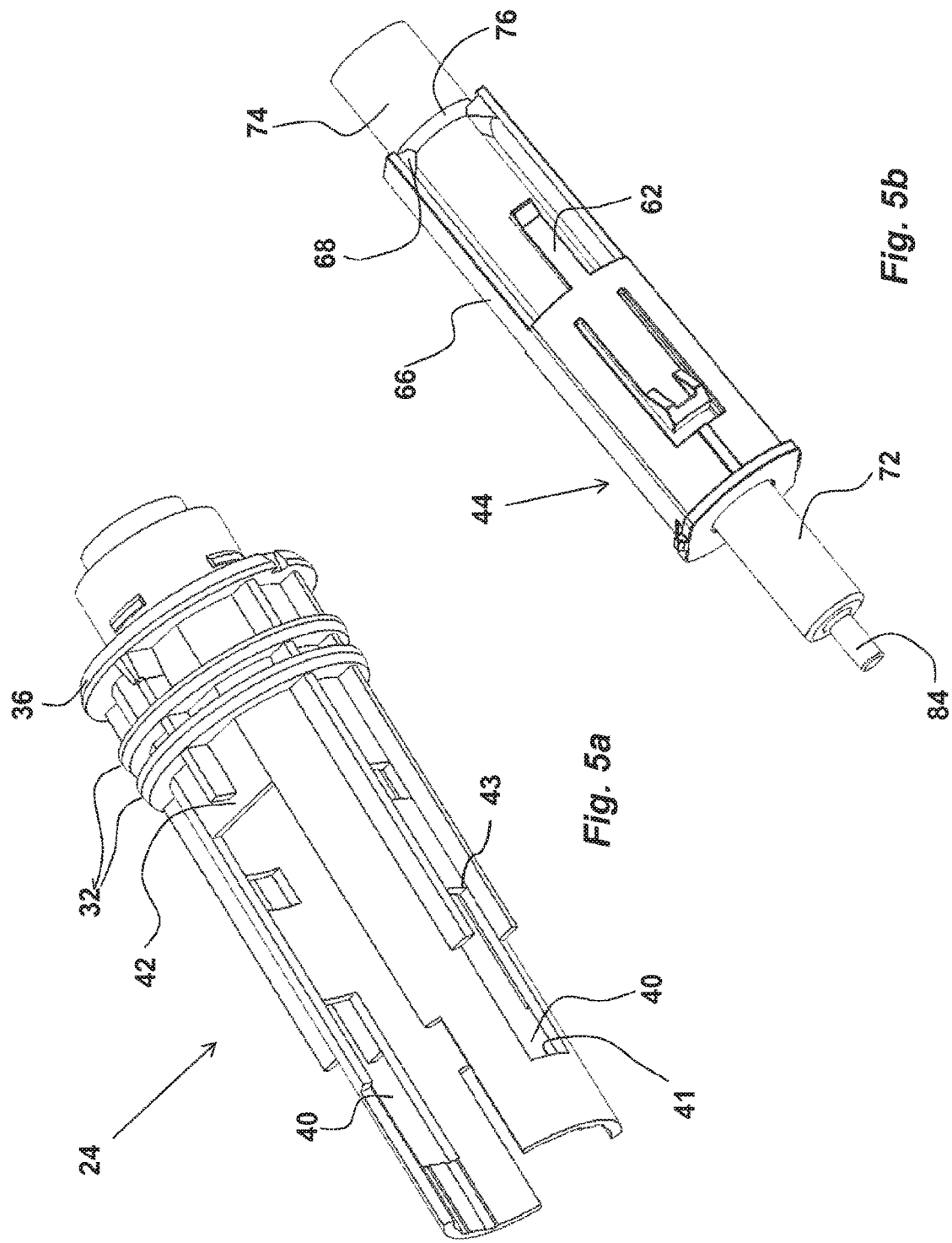

The power unit 20, FIGS. 4-5, comprises a generally tubular body, hereafter named power body 24. At a distal end of the power body, the end cap 26 is attached with suitable attachment means. In the embodiment shown the attachment means comprises radially outwardly extending protrusions 28 on a side surface of the power body 24, cooperating with an annularly extending groove 30 on an inner surface of the end cap 26. The power body 24 is further arranged with annularly extending ledges 32, FIG. 5a, which ledges 32 are arranged to cooperate with circumferential grooves 34, FIG. 9, on an inner surface of the distal end of the housing 10 to fix the power body to the housing. A further ledge 36 on the power body is designed to abut a distally directed end surface 38, FIG. 9 of the housing 10 when the power body 24 is attached to the housing 10.

The power body 24 comprises a cylindrical wall 42 and two cut-outs extending in the longitudinal direction L forming two longitudinally extending surfaces towards the proximal end. Each longitudinally extending surface comprises an elongated opening 40. Each elongated opening 40 is arranged with a holding element, hereinafter called fourth holding element 41 and with a blocking element, hereinafter called second blocking element 43. In the embodiment shown, the fourth holding element 41 is arranged as a transversal and distally directed end contact surface positioned at the proximal end of the elongated opening 40 and the second blocking element 43 is arranged as a transversal and proximally directed end contact surface positioned at the distal end of the elongated opening 40.

Figure 6:
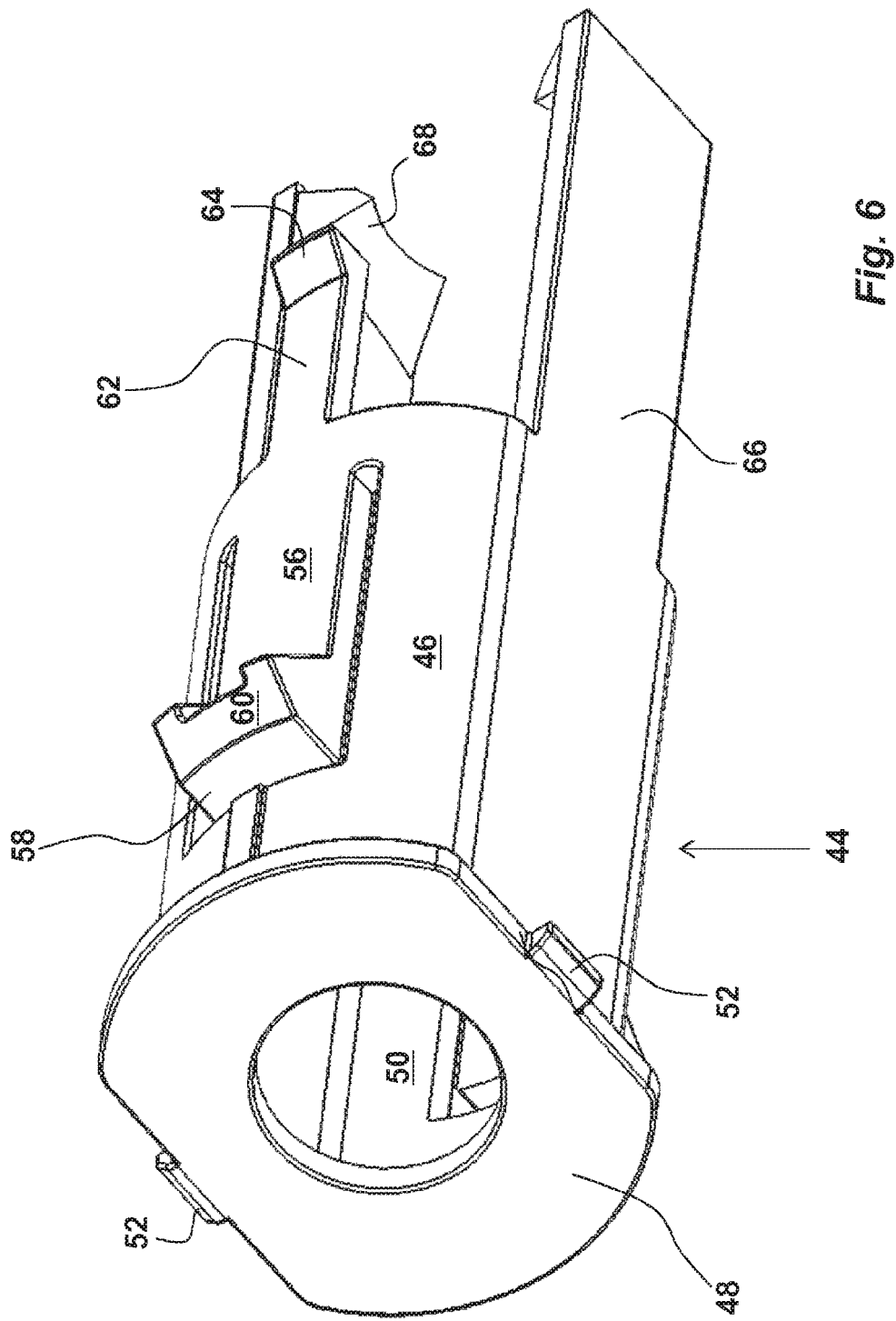
Figure 7:
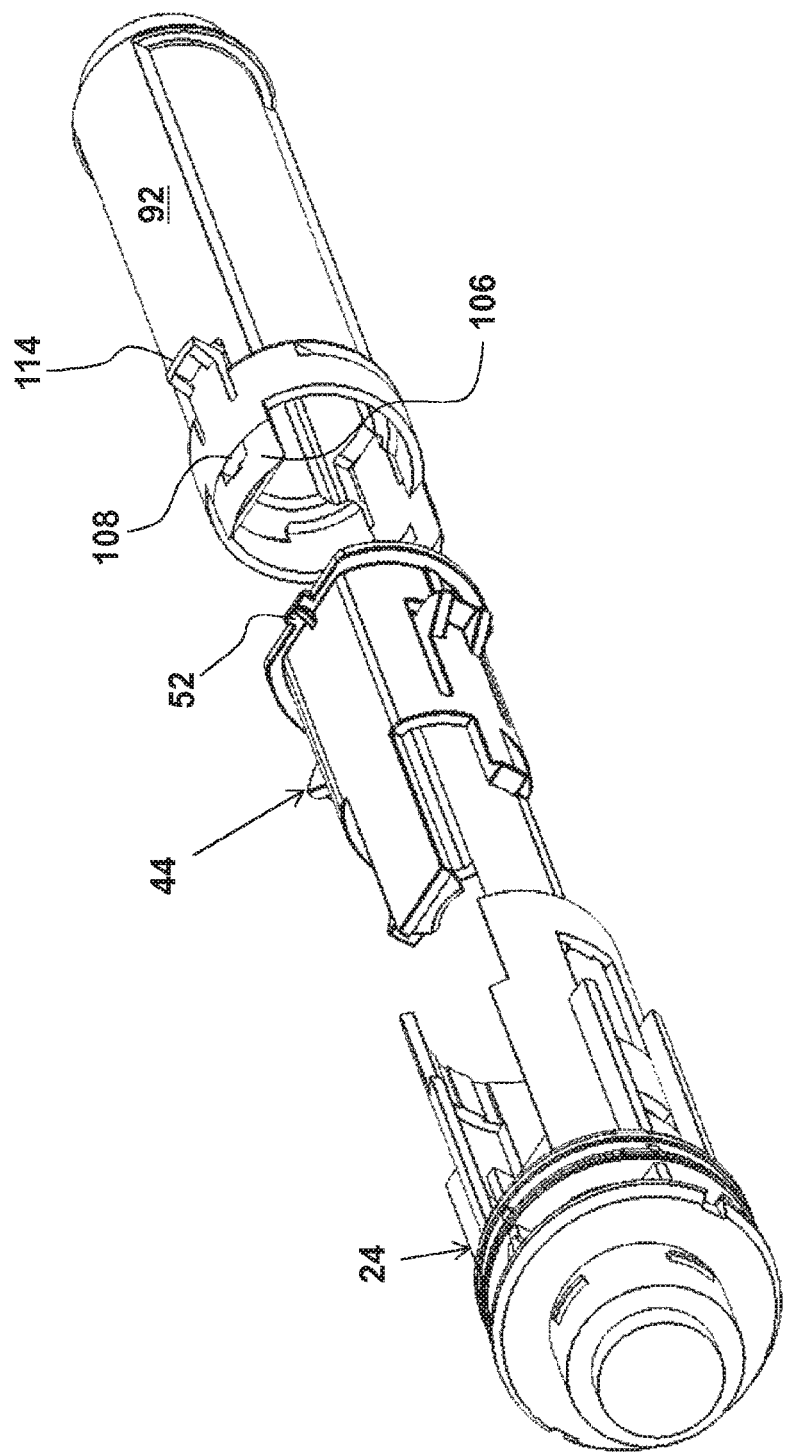

The power unit 20 further comprises a plunger rod driver 44, FIGS. 5 and 6, which is arranged inside the power body 24 and coaxially movable therewith. The plunger rod driver 44 comprises a generally tubular body 46. A proximal end of the body 46 is arranged with an end surface 48 having a central, generally circular, passage 50, FIG. 6. A side edge of the end surface 48 is arranged with two first attachment elements 52, in the embodiment shown arranged as locking protrusions positioned generally on opposite side edges of the end surface. The body 46 of the plunger rod driver is further arranged with third holding elements 56, which in the embodiment shown are arranged as flexible tongues having a free end directed towards the proximal end of the device. The third holding elements 56 are placed generally on opposite sides of the tubular body 46. Each third holding element 56 i.e. tongue comprises generally outwardly extending protrusions 58 positioned on the free end. Each protrusion 58 is arranged with an inclined surface 60 as seen in FIG. 6.

The body 46 is further arranged with first blocking elements 62, in the embodiment shown arranged as distally directed flexible arms, extending from an end surface of the body 46 and placed generally in line with the third holding elements 56 as seen in a longitudinal direction. Each first blocking element 62 in the shown embodiment comprises a protrusion 64 having a generally wedge-shaped form and extending radially outwards as seen from the side. The body 46 is further arranged with first holding elements 66 in the embodiment shown arranged as distally directed flexible arms extending from the end surface of the body. Each first holding element 66 comprises a protrusion 68 having a wedge-shape in cross-section and extending radially inwards as seen in FIG. 6. The distal ends of the first holding elements 66 are designed to fit into the wall 42 of the power body 24, FIG. 3a, for blocking movement of the first holding elements 66 in the radial outward direction.

Figure 2:
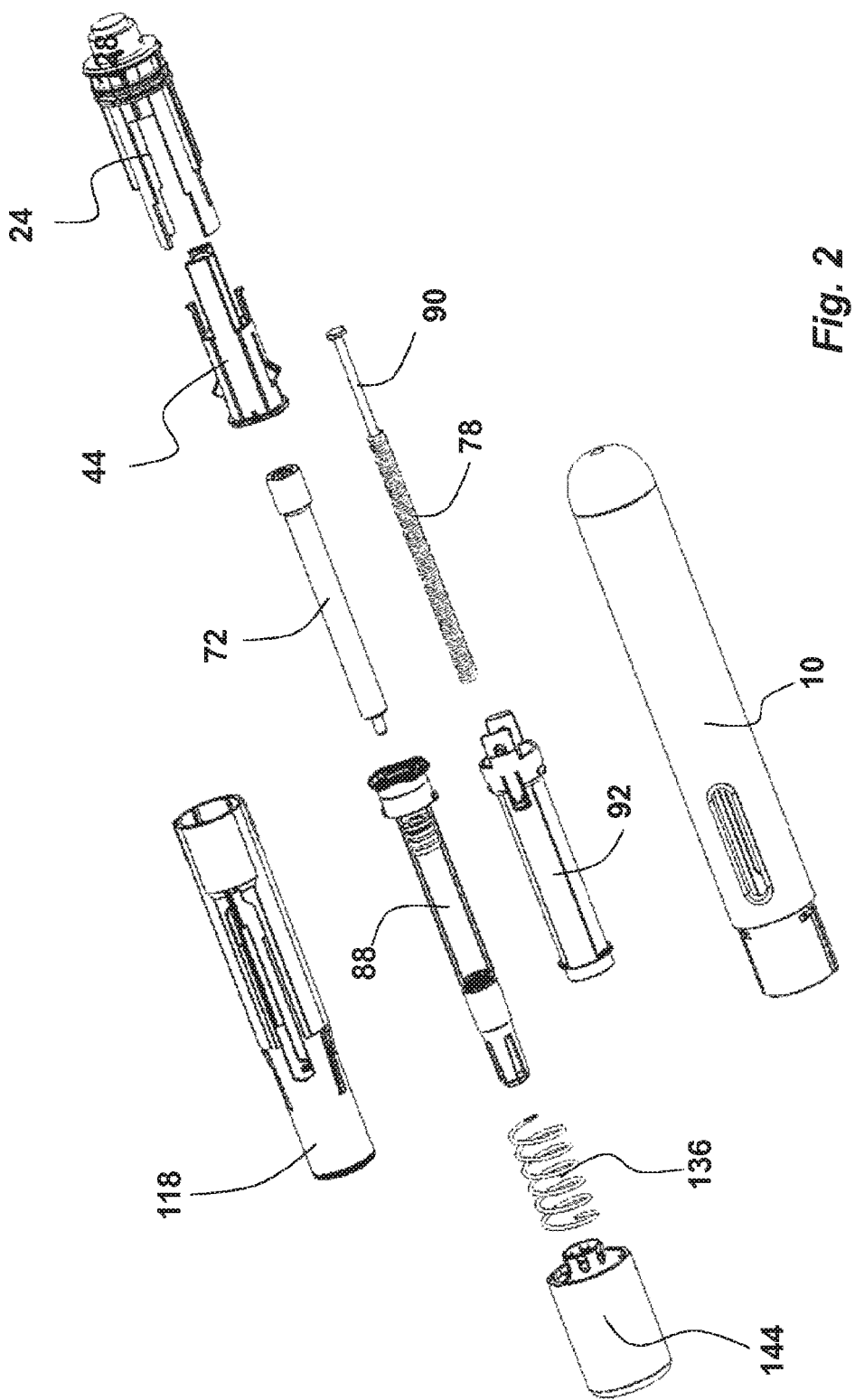
FIG. 2 is an exploded view of the embodiment of FIG. 1, FIGS. 3a, 3b are cross-sectional longitudinal views of the device of FIG. 1, taken 90 degrees in relation to each other.
Figure 3:
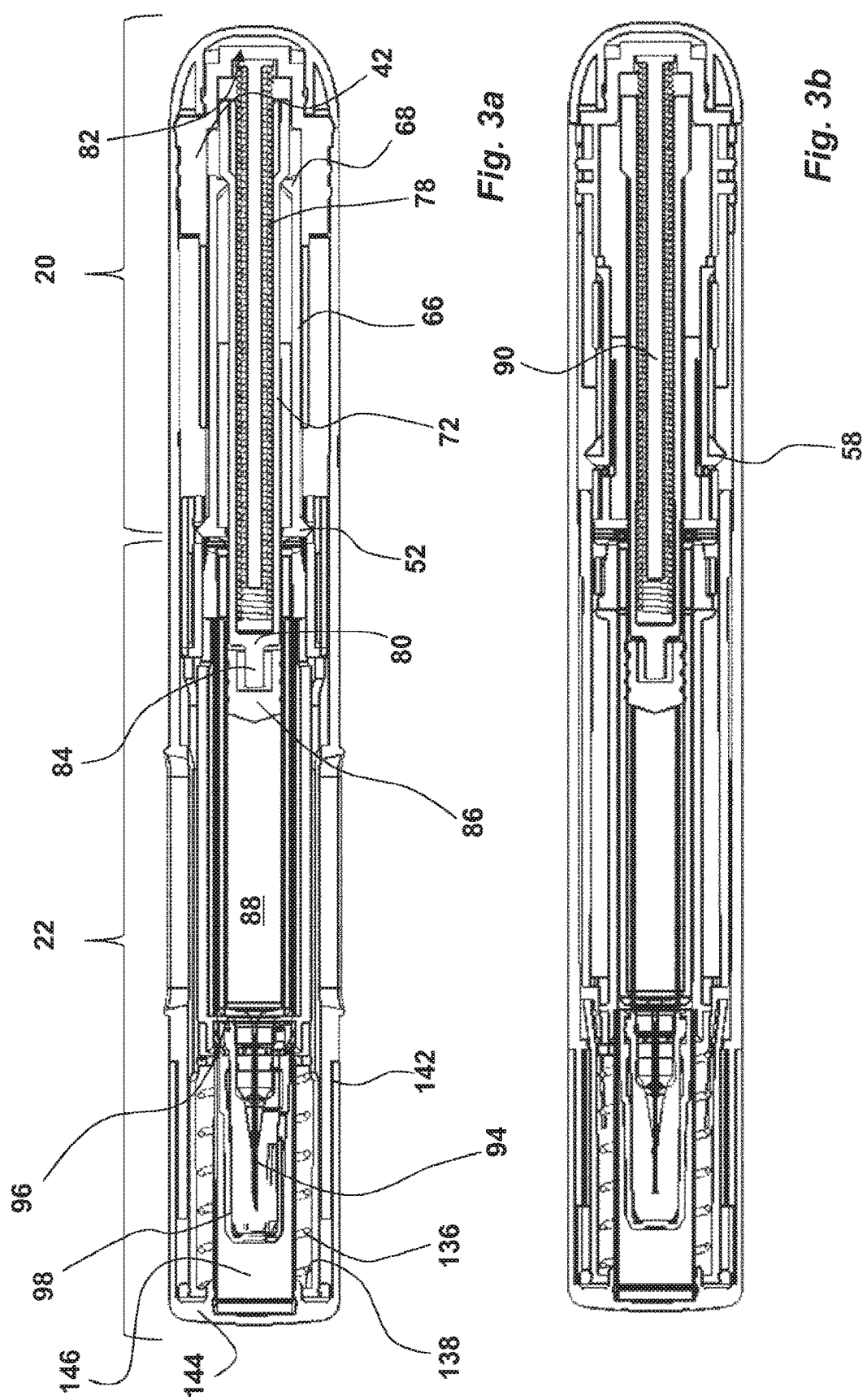

The power unit 20 further comprises a generally elongated plunger rod 72 having a generally circular cross-section with a first diameter, FIG. 5b. A distal area 74 of the plunger rod is provided with a second diameter, which is larger than the first diameter. The plunger rod comprises a second holding element 76, which in the embodiment shown is a contact surface between the first and the second diameter. Said contact surface is inclined in relation to a normal to the longitudinal direction L. The second holding element 76 is intended to cooperate with the inclined wedge-shaped protrusions 68 of the first holding elements 66 on the plunger rod driver 44. A plunger rod drive member or force spring element 78, FIGS. 2 and 3 is further arranged in an elongated cavity inside the plunger rod 72. In the embodiment shown the force spring element 78 is a compression spring that in the assembled state of the power unit is compressed between an end wall 80 at the proximal end of the plunger rod 72 and a proximally directed surface 82 of the power body 24, FIG. 3. The proximal end of the plunger rod may be provided with a pin 84 or guide intended to fit into a passage in a movable stopper 86 of a medicament container 88, FIG. 3a, comprised in the medicament delivery unit 22. The medicament container 88 is arranged with a transversally extending ledge 89 at its distal end. A guide pin 90, FIG. 3b, is further arranged inside the compression spring 78 for preventing buckling thereof.

Figure 8:
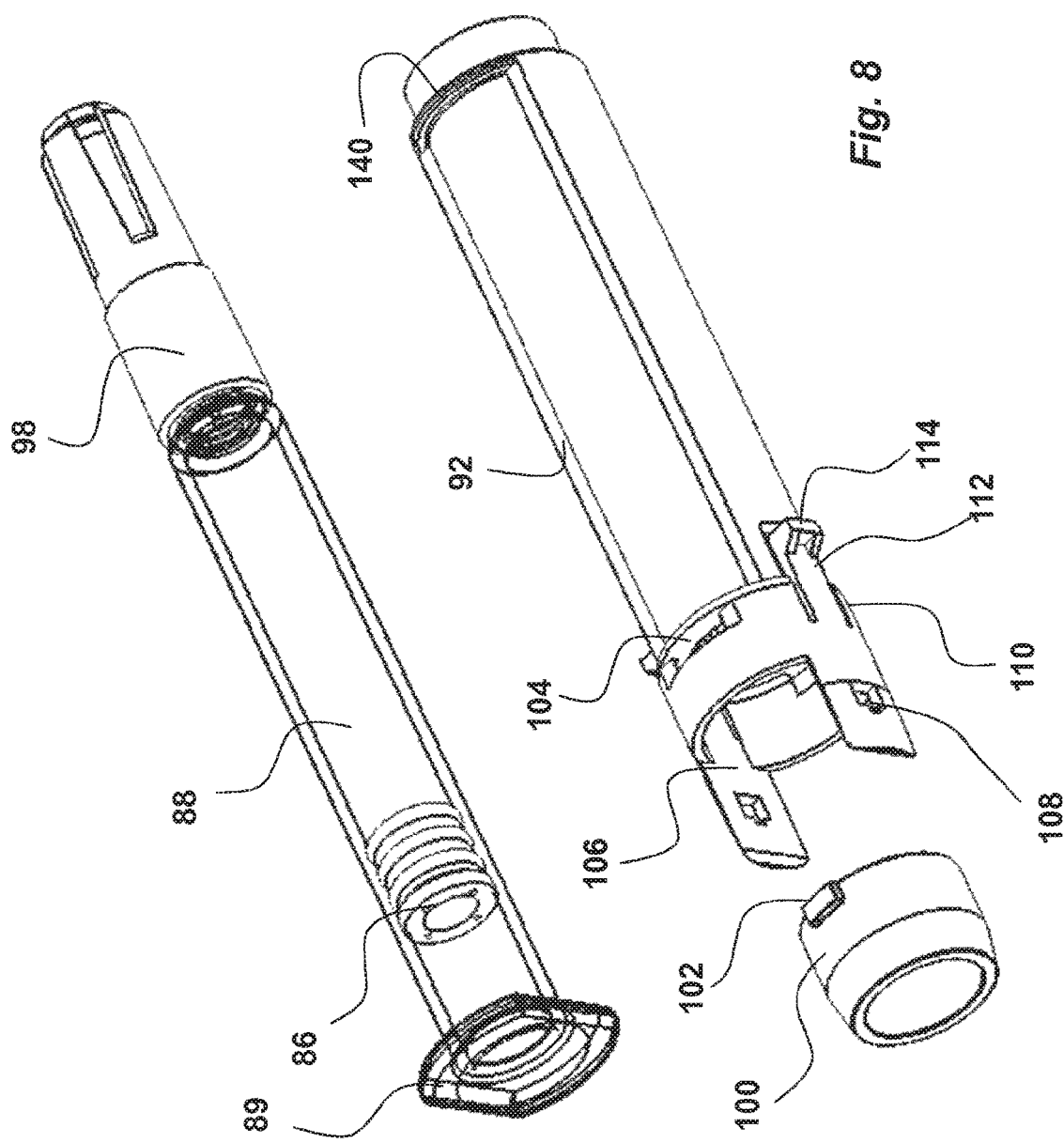

The medicament container 88 with its stopper 86 comprised in the medicament delivery unit is intended to be inserted into a generally tubular elongated medicament container holder 92, FIG. 8 from a distal end thereof. The medicament container 88 may be provided with a medicament delivery member 94, FIG. 3a, such as an injection needle, either integrated or attached. The medicament delivery member, preferably provided with a guard 98, protrudes through the ring-shaped wall. The guard may be of any suitable design, such as a rigid needle shield or RNS that is shown in the drawings. The medicament container 88 is preferably made of a transparent material so that the medicament is visible. The medicament container 88 is arranged with a transversal ledge or flange 89, FIG. 8, at its distal end.

A damping element 100 is connected to the distal end of the medicament container via outwardly directed protrusions 102 on its outer surface fitting into cut-outs 104 in the medicament container holder. The medicament container holder 92 is further arranged with second attachment elements 106 e.g. distally directed flexible arms extending from an end surface thereof. Each second attachment element 106 is arranged with a cut-out, recess or passage 108, which cooperate with each first attachment element 52, e.g. protrusion of the plunger rod driver 44 of the embodiment, whereby the power unit 20 is connected to the medicament delivery unit 22. The medicament container holder 92 is further arranged with generally U-shaped cut-outs 110 forming tongues 112 having free ends facing the proximal direction. The free ends of the tongues 112 are arranged with radially outwards directed protrusions 114, where proximally directed surfaces of the protrusions 114 are intended to cooperate with distally directed ledges 116 on an inner surface of the housing, FIG. 9. In the embodiment shown, the ledges 116 are adjacent a distal end of the window 16 of the housing 10. Preferably the medicament container holder is designed in a transparent material such that the medicament container 88 and its content are visible.

Figure 9:
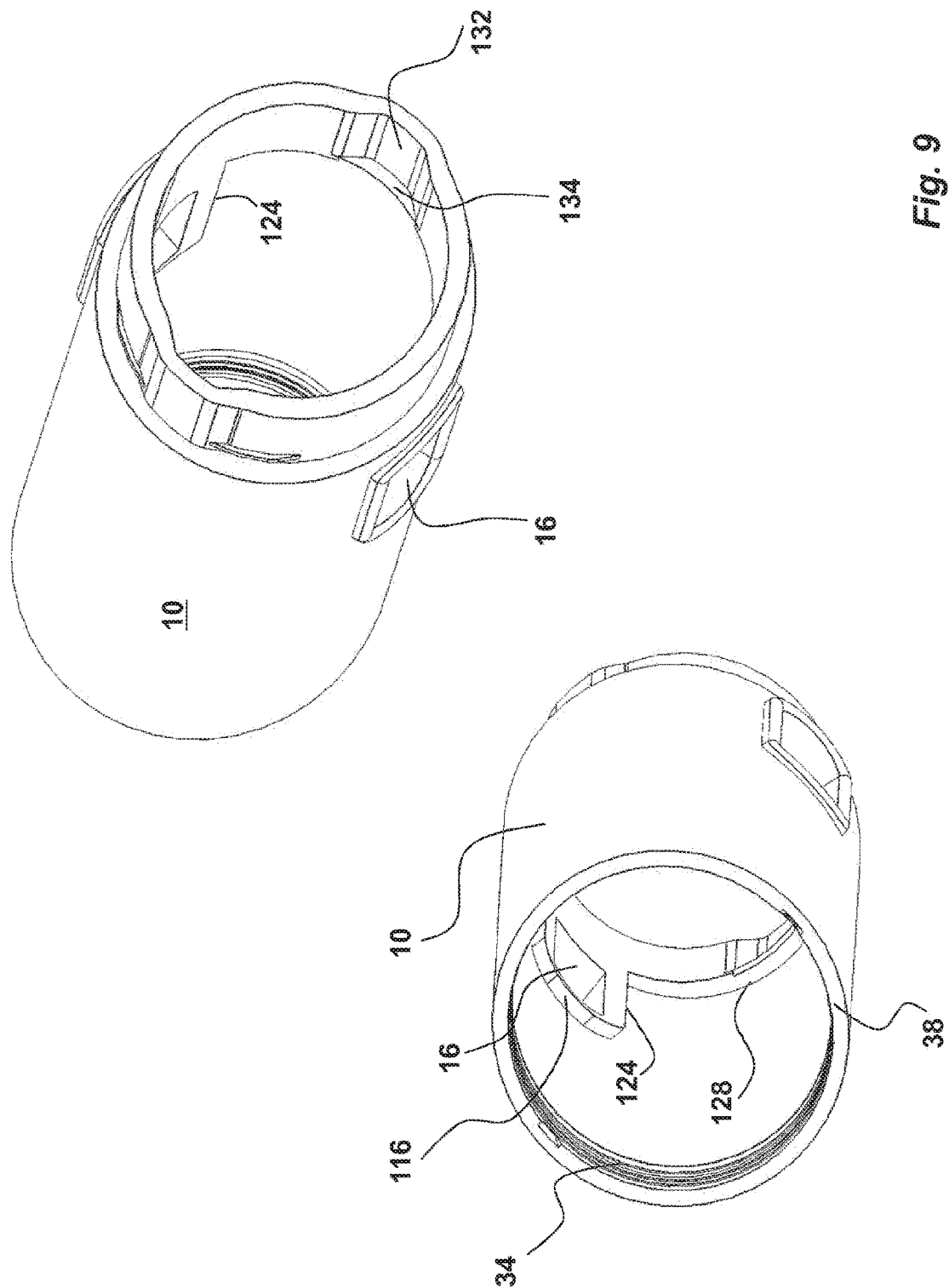
Figure 10:
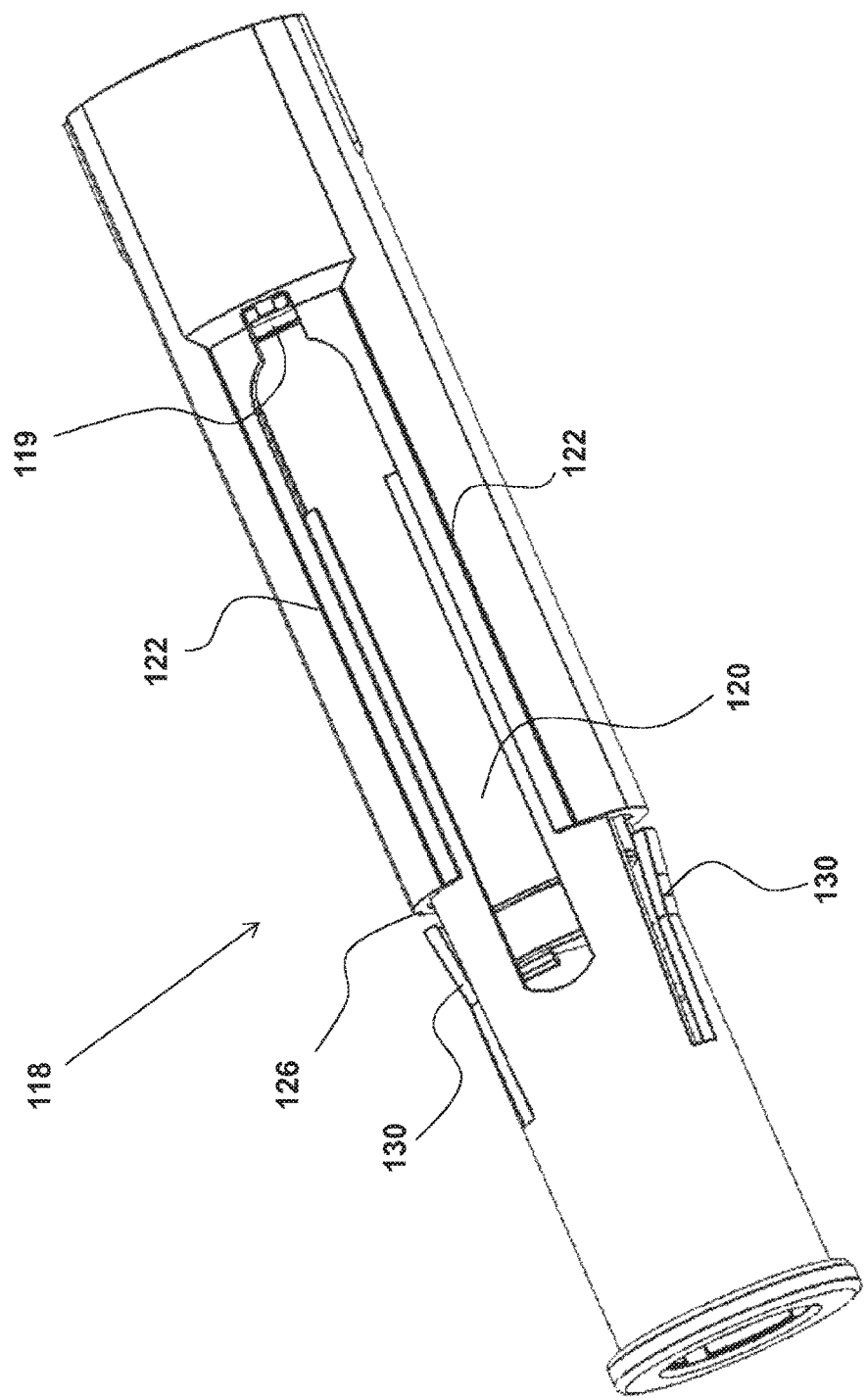

The medicament delivery unit further comprises a medicament delivery member shield 118, FIGS. 2 and 10, arranged movable in the longitudinal direction in relation to the housing. In this respect, the medicament delivery member shield 118 is arranged as a generally tubular body having a diameter somewhat smaller than the inner diameter of the housing 10. The medicament delivery member shield 118 is provided with elongated openings 120, through which the medicament container is visible. The openings are arranged with proximally directed end surfaces 119, FIG. 10. Also the protrusions 114 of the tongues 112 of the medicament container holder 92 are arranged to protrude through the openings 120. The medicament delivery member shield 118 is also provided with longitudinally extending guide surfaces 122 on each side of the opening 120, which guide surfaces cooperate with longitudinally extending ledges 124, FIG. 9, on an inner surface of the housing 10 on each side of the windows thereof.

The medicament delivery member shield 118 is further arranged with a proximally directed ledge 126, which is intended to cooperate with distally directed ledges 128, FIG. 9, of the inner surface of the housing 10. Also, the medicament delivery member shield 118 is arranged with flexible first locking elements 130 that have their free ends in the distal direction. The flexible first locking elements 130 in the present embodiment are tongues which are designed with a certain outwards inclination in relation to the longitudinal direction. The flexible first locking elements 130 are arranged extending in a generally distal direction and are operably engageable with second locking elements 132 arranged on the inner surface of the housing 10. The second locking elements 132 in the present embodiment are recesses on the inner surface of the proximal area of the housing, FIG. 10. The recesses are provided with proximally directed end surfaces 134. The first and said second locking elements are arranged to engage and lock the medicament delivery member shield 118 when the medicament delivery member shield force element 136 has urged said medicament delivery member shield 118 in the proximal direction after medicament delivery, thereby shielding said medicament delivery member 94.

The free ends of the flexible first locking elements 130 are positioned inside the second locking elements 132 e.g. recesses on the inner surface of the proximal area of the housing, FIG. 10. The second locking elements 132 e.g. recesses are provided with proximally directed end surfaces 134. The medicament delivery member shield 118 is further arranged with a medicament delivery member shield force element 136 which in the embodiment shown is a compression spring, FIG. 3. The compression spring is fitted between a distally directed end surface 138 of the medicament delivery member shield, FIG. 3, and a proximally directed ledge surface 140, FIG. 8, of the medicament container holder 92.

The protective cap 18 is also provided to the device, having a generally tubular shape with an end wall 144, FIG. 3. A delivery member guard remover 146 is arranged to the protective cap 18. In the embodiment shown the delivery member guard remover 146 is arranged as a tubular member attached to an inner surface of the end wall 144, surrounding the delivery member guard 98. The remover is provided with grip member capable of gripping the guard 98 as will be explained.

When the device is delivered to the user, the power unit is in the assembled state which means that the force spring element 78 is compressed such that the plunger rod 72 and the force spring element 78 are held in an injection tensioned state by the plunger rod driver 44, the plunger rod driver 44 is held in a penetration tensioned state by the power body 24 and the power body is fixedly connected to the housing. The plunger rod driver 44 is coaxially arranged within the power body 24 such that the wall 42 of the power body prevents the first holding elements 66 of the plunger rod driver 44 to flex radially outwards whereby the protrusion 68 is held in contact with the second holding element 76 i.e. contact surface of the plunger rod for holding the plunger rod 72 and said force spring element 78 in the injection tensioned state. Also, the third holding elements 56 of the plunger rod driver 44 are in contact with the fourth holding element 41 i.e. contact surface of the power body 24 for holding the plunger rod driver 44 in the penetration tensioned state. The medicament container 88 is mounted in the medicament container holder and is held in place by its ledge 89 positioned between a distally directed surface of the dampening member 100 and a proximally directed surface of the plunger rod driver 44. The medicament delivery unit is connected to the power unit.

When the device is to be used, the protective cap 18 is removed. The removal causes the needle shield remover 146 to grip and pull the needle shield 98 from the medicament delivery member 94. The device is now ready to be used, see FIG. 11. The medicament delivery member 94 is now inside the medicament delivery member shield 118, but the medicament delivery member shield 118 is free to move in relation to the housing 10. The medicament delivery member shield 118 is however urged in the proximal direction by the medicament delivery member shield force element 136 where the extended position is limited by the protrusions 114 of the medicament container holder 92 resting on the proximally directed end surface 119 of the openings 120 of the medicament delivery member shield 118. The user then presses the proximal end of the medicament delivery member shield 118 against a dose delivery site on the patient, whereby the medicament delivery member shield 118 is moved in the distal direction inside the housing. The movement also causes the medicament delivery member shield force element 136 to be tensioned.

A distally directed end surface of the medicament delivery member shield 118 will come in contact with the third holding elements 56 which are resting on the fourth holding elements 41. The action of the medicament delivery member shield 118 on the third holding element 56 will force them generally inwards whereby the plunger rod driver 44 is released from the penetration tensioned state. Due to the compressed state of the force spring element 78, providing a force on the plunger rod 72 in the proximal direction, and due to that the plunger rod 72 is locked to the plunger rod driver 44 by the first holding elements 66, being in contact with the second holding element 76, both the plunger rod 72 and the plunger rod driver 44 will be forced in the proximal direction. The first holding elements 66 are held in that position by the wall 42 of the power body. Due to the connection of the first and second attachment elements, enabling attachment of the plunger rod driver 44 with the medicament container holder 92 by the first attachment elements 52 e.g. protrusions fitting into the with the second attachment elements 106, e.g. distally directed flexible arms with cut-outs, also the medicament container holder 92 and thus the medicament container 88 with its medicament delivery member 94 will be moved in the proximal direction, whereby a penetration of the medicament delivery member into the tissue of the patient is performed, FIGS. 12a, b. The medicament delivery member shield force element 136 is compressed further during the movement in the distal direction of the medicament delivery member shield 118. After or direct after the plunger rod driver is released from the penetration tensioned state, the first blocking elements 62 are moved out into the openings 40 of the power body 24, FIG. 13b, such that the medicament container holder 92 and the plunger rod driver 44 are prevented i.e. blocked from moving in the distal direction by the medicament delivery member shield force element 136, more particularly, the first blocking elements 62 come into contact with the second blocking elements 43 such that the protrusions 64 of the first blocking elements 62 are in contact with the second blocking elements 43 e.g. proximally directed end surfaces of the elongated openings 40 of the power body 24, FIG. 14b.

When the medicament container has moved a certain distance in the proximal direction, corresponding to a certain penetration depth, the movement of the medicament container 88 is stopped in that the protrusions 114 of the arms 112 of the medicament container holder 92 are moved in contact with the distally directed ledges 116 on the inner surface of the housing 10. Just before this position the plunger rod driver 44 and the plunger rod 72 has moved in relation to the power body 24 such that the first holding elements 66 e.g. flexible arms of the plunger rod driver 44 pass out of the wall 42 of the power body 24, FIG. 12a of the embodiment. The first holding elements 66 are then free to move radially outwards whereby the first holding elements 66 of the plunger rod driver are moved out of contact with the second holding element 76 e.g. contact surface of the plunger rod 72, i.e. releasing the plunger rod 72 with said force spring element 78 from the injection tensioned state.

The plunger rod 72 is now free to move in the proximal direction by itself due to the force of the force spring element 78. The medicament container holder 92 now is held stationary due to the interaction between the first blocking elements 62 with the second blocking elements 43 and the interaction between the protrusions 114 of the arms 112 of the medicament container holder 92 with the distally directed ledges 116 on the inner surface of the housing 10. The movement of the plunger rod 72 now causes the stopper 86 to be moved proximally inside the medicament container, which in turn causes a dose of medicament to be delivered through the medicament delivery member, FIG. 13.

When the injection sequence has ended the device may be withdrawn from the dose delivery site. The medicament delivery member shield force element 136 that is compressed between the ledge surface 138 of the medicament delivery member shield 118 and the surface 140 medicament container holder can now push the medicament delivery member shield in the proximal direction, FIG. 14. The medicament delivery member shield is stopped in its most proximal position, shielding the injection needle, when the proximally directed end surface 119 of the elongated opening 120 of the medicament delivery member shield 118 is moved in contact with a distally directed surface of the protrusions 114 of the medicament container holder 92, FIG. 14a, which protrusions 114 are in contact with the ledge 116 of the housing as explained above.

The first locking elements 130 of the medicament delivery member shield 118 have now been moved such that their free ends are positioned in contact with the second locking elements, i.e. the recesses of the housing of the embodiment, whereby the distally directed end surfaces of the arms are in contact with the proximally directed end surfaces 134 of the second locking elements 132. This effectively locks the medicament delivery member shield in the extended, shielding position. The device may now be discarded.

It is to be understood that the elements described above and shown in the drawings are only examples of structures that may be replaced by other elements displaying the same or similar function for obtaining the desired end result. Further it is to be understood that the embodiment described above and shown in the drawings only is to be regarded as comprising a non-limiting example of the invention and that it may be modified in many ways within the scope of the patent claims.

The invention claimed is:

1. A power unit for a medicament delivery device comprising:
   a power body having opposite proximal and distal ends,
   a plunger rod driver coaxial and movably arranged in relation to said power body,
   a plunger rod coaxial and movably arranged in relation to said plunger rod driver,
   a force spring element operably connected between said plunger rod and said power body;
   wherein the plunger rod driver comprises:
   a first holding element arranged to interact with a second holding element on said plunger rod and with a wall of the power body for releasably holding said plunger rod with said force spring element in an injection tensioned state;
   a third holding element arranged to interact with a fourth holding element on said power body for releasably holding said plunger rod driver in a penetration tensioned state;
   a first attachment element arranged to interact with a second attachment element on a medicament container holder, capable of attaching the two attachment elements together; and
   a first blocking element arranged to mechanically interact with a second blocking element located on said power body after the plunger rod driver is released from the penetration tensioned state, where the first blocking element moves radially outward to contact and engage the second blocking element such that movement of said plunger rod driver in the distal direction is blocked.

2. The power unit according to claim 1, wherein said first attachment element comprises at least one locking protrusion and wherein said second attachment member comprises at least one flexible arm provided with a recess, arranged to accommodate said at least one locking protrusion.

3. The power unit according to claim 1, wherein said first holding element comprises a distally directed flexible arm having a protrusion and wherein said second holding element comprises a contact surface.

4. The power unit according to claim 3, wherein said third holding element comprises a flexible tongue having a protrusion and wherein said fourth holding element comprises a transversal and distally directed end contact surface provided on an elongated opening on the power body.

5. The power unit according to claim 4, wherein the plunger rod driver is configured to be coaxially arranged within the power body such that the wall of the power body prevents the first holding element of the plunger rod driver to flex radially outwards whereby the protrusion of the first holding element is held in contact with the second holding element for holding the plunger rod and said force spring element in the injection tensioned state and wherein the third holding element of the plunger rod driver is configured to be resting on the forth holding element of the power body for holding the plunger rod driver in the penetration tensioned state.

6. The power unit according to claim 1, wherein said first blocking element comprises a flexible arm having a protrusion and wherein said second blocking element comprises a transversal and proximally directed end contact surface provided on an elongated opening of the power body.

7. A medicament delivery device according to claim 1, comprising said power unit, wherein the power unit is arranged inside a generally tubular housing having opposite proximal and distal ends along a longitudinal axis, said medicament delivery device further comprising:
a medicament container holder capable of supporting a medicament container provided with a medicament delivery member, which medicament container comprises a chamber containing a medicament, and an axially movable stopper; as well as
a generally tubular medicament delivery member shield coaxially and slidably arranged within the housing, and
a medicament delivery member shield force element, operably arranged to force said medicament delivery member shield in the proximal direction.

8. The medicament delivery device according to claim 7, wherein the generally tubular medicament delivery member shield is configured to interact with the third holding element which is resting on the fourth holding element when the tubular medicament delivery member shield is moved in the distal direction in relation to the housing such that the third holding element is forced to move generally inwards whereby the plunger rod driver is released from the penetration tensioned state.

9. The medicament delivery device according to claim 8, wherein the plunger rod driver together with the plunger rod are movable in relation to the power body such that after the plunger rod driver is released from the penetration tensioned state, the first blocking element are moved out into openings of the power body for interacting with the second blocking element whereby the medicament container holder and the plunger rod driver are prevented from moving in the distal direction by the medicament delivery member shield force element.

10. The medicament delivery device according to claim 8, wherein the plunger rod driver together with the plunger rod are movable in relation to the power body such that after the plunger rod driver is released from the penetration tensioned state, the first holding element of the plunger rod driver are moved out of the wall of the power body and flexed radially outwards whereby the first holding element of the plunger rod driver are moved out of contact with the second holding element for releasing the plunger rod with said force spring element from the injection tensioned state.

11. The medicament delivery device according to claim 10, further comprising:
flexible first locking elements arranged on said medicament delivery member shield, which flexible first locking elements are arranged extending in a generally distal direction, operably engageable with second locking elements arranged to said housing, wherein said first and said second locking elements are arranged to engage and lock said medicament delivery member shield when said medicament delivery member shield force element has urged said medicament delivery member shield in the proximal direction after medicament delivery, thereby shielding said medicament delivery member.

12. The medicament delivery device according to claim 11, wherein said first locking elements comprise at least two tongues having free ends being flexible in a direction which is generally perpendicular to the longitudinal axis.

13. The medicament delivery device according to claim 12, wherein said first locking elements are arranged with a certain inclination which extend outwardly in relation to the longitudinal axis.

14. The medicament delivery device according to claim 11, wherein said second locking element comprises at least one proximally directed ledge portion having one recess into which said first locking elements fit for engagement.

15. A power unit for a medicament delivery device comprising:
a power body having opposite proximal and distal ends,
a plunger rod driver coaxial and movably arranged in relation to the power body,
a plunger rod coaxial and movably arranged in relation to the plunger rod driver,
a force spring element operably connected between the plunger rod and the power body;
wherein the plunger rod driver comprises:
a first holding element arranged to interact with a second holding element on the plunger rod and with a wall of the power body for releasably holding the plunger rod with the force spring element in an injection tensioned state;
a third holding element arranged to interact with a fourth holding element on the power body for releasably holding the plunger rod driver in a penetration tensioned state;
a first attachment element arranged to interact with a second attachment element on a medicament container holder, capable of attaching the two attachment elements together, wherein the first attachment element comprises at least one locking protrusion and wherein the second attachment member comprises at least one flexible arm provided with a recess, arranged to accommodate the at least one locking protrusion; and
a first blocking element arranged to interact with a second blocking element on the power body, for blocking any movement of the plunger rod driver in the distal direction after the plunger rod driver is released from the penetration tensioned state.

16. A power unit for a medicament delivery device comprising:
a power body having opposite proximal and distal ends,
a plunger rod driver coaxial and movably arranged in relation to the power body,
a plunger rod coaxial and movably arranged in relation to the plunger rod driver,
a force spring element operably connected between the plunger rod and the power body;
wherein the plunger rod driver comprises:
a first holding element arranged to interact with a second holding element on the plunger rod and with a wall of the power body for releasably holding the plunger rod with the force spring element in an injection tensioned state;

a third holding element arranged to interact with a fourth holding element on the power body for releasably holding the plunger rod driver in a penetration tensioned state;

a first attachment element arranged to interact with a second attachment element on a medicament container holder, capable of attaching the two attachment elements together; and a first blocking element arranged to interact with a second blocking element on the power body, for blocking any movement of the plunger rod driver in the distal direction after the plunger rod driver is released from the penetration tensioned state, wherein the first blocking element comprises a flexible arm having a protrusion and wherein the second blocking element comprises a transversal and proximally directed end contact surface provided on an elongated opening of the power body.

* * * * *